(12) United States Patent
Rohner et al.

(10) Patent No.: US 10,863,904 B2
(45) Date of Patent: Dec. 15, 2020

(54) RECORDING DEVICE

(71) Applicant: Ivoclar Vivadent AG, Schaan (LI)

(72) Inventors: Gottfried Rohner, Altstätten (CH);
Ronny Watzke, Feldkirch (AT);
Theresa Senti, Schaanwald (LI);
Antonio Ferilli, Waengi (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 16/320,820

(22) PCT Filed: Jul. 25, 2017

(86) PCT No.: PCT/EP2017/068753
§ 371 (c)(1),
(2) Date: Jan. 25, 2019

(87) PCT Pub. No.: WO2018/019826
PCT Pub. Date: Feb. 1, 2018

(65) Prior Publication Data
US 2019/0167107 A1 Jun. 6, 2019

(30) Foreign Application Priority Data

Jul. 29, 2016 (EP) ..................................... 16181975

(51) Int. Cl.
*A61B 5/00* (2006.01)
*A61B 1/00* (2006.01)
(Continued)

(52) U.S. Cl.
CPC ........ *A61B 5/0062* (2013.01); *A61B 1/00082* (2013.01); *A61B 1/00172* (2013.01);
(Continued)

(58) Field of Classification Search
CPC ............ A61B 1/00082; A61B 1/00172; A61B 5/0062; A61B 5/1079; A61B 5/682; A61C 9/0053
See application file for complete search history.

(56) References Cited

U.S. PATENT DOCUMENTS

| | | |
|---|---|---|
| 5,451,232 A | 9/1995 | Rhinehart |
| 5,785,051 A | 7/1998 | Lipscher et al. |

(Continued)

FOREIGN PATENT DOCUMENTS

| | | |
|---|---|---|
| JP | 2000-126122 A | 5/2000 |
| WO | 02/00115 A1 | 1/2002 |

*Primary Examiner* — Dani Fox
(74) *Attorney, Agent, or Firm* — Ann M. Knab; Thad McMurray

(57) ABSTRACT

The invention relates to a recording device (10) comprising a scan head carrier (18) for moving the scan head (20) across a scan area (42) of a cavity, the scan area (42) extending around the scan head (20). A flat or film-like, elastically stretchable material extends between the scan head (20) and the scan area (42), which material can be pressed against the scan area (42) in a balloon (12)-type manner using overpressure. The scan head guide (18) passes through the balloon outlet (16) of the balloon (12) towards the scan head (20). In particular, a control device (44) determines the shape of the cavity (40) against which the material is pressed, from deformation of the material when applying said overpressure. A second extraoral scanning head (43) scans deformations during pressurization of the film-like material.

15 Claims, 1 Drawing Sheet

(51) Int. Cl.
*A61C 9/00* (2006.01)
*A61B 1/24* (2006.01)
*A61B 5/107* (2006.01)
*A61B 1/05* (2006.01)

(52) U.S. Cl.
CPC .................. *A61B 1/05* (2013.01); *A61B 1/24* (2013.01); *A61B 5/0084* (2013.01); *A61B 5/1076* (2013.01); *A61B 5/1077* (2013.01); *A61B 5/1079* (2013.01); *A61B 5/682* (2013.01); *A61C 9/0053* (2013.01)

(56) References Cited

U.S. PATENT DOCUMENTS

| | | |
|---|---|---|
| 2006/0241345 A1 | 10/2006 | Oishi et al. |
| 2010/0222706 A1 | 9/2010 | Miyahara et al. |
| 2014/0276105 A1 | 9/2014 | De Brouchoven |
| 2014/0330133 A1* | 11/2014 | Stern .................. A61B 5/6853 600/479 |

* cited by examiner

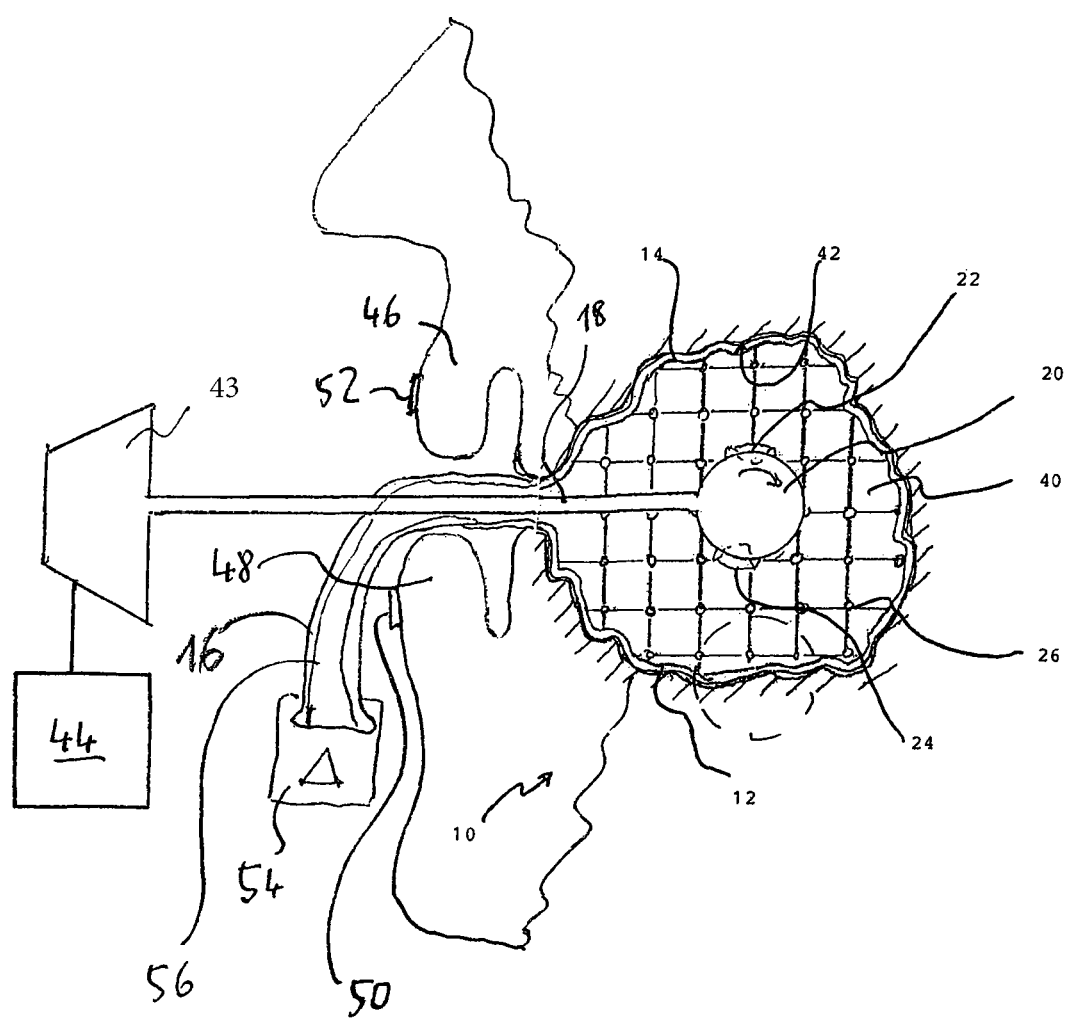

RECORDING DEVICE

CROSS-REFERENCE TO RELATED APPLICATIONS

This application is a National Stage application of International patent application PCT/EP2017/068753 filed on Jul. 25, 2017, which claims priority to European patent application No. 16181975.0 filed on Jul. 29, 2016, the disclosures of which are incorporated herein by reference in their entirety.

FIELD OF THE INVENTION

The invention relates to a recording device as well as a method for operating a recording device.

BACKGROUND OF THE INVENTION

It is known per se to arrange balloons that can be inflated around recording coils for evaluating measurement signals. Inflation is done through the balloon outlet which is also passed by the connecting lines for the sensor.

For the medical sector, such a solution can be found for example in DE 42 33 809 A1, but also for example in WO 2014/145058A1. Such solutions allow protection of sensitive sensor elements and are used, for example, to analyze auditory canals.

In some cases it is desirable to detect the internal structure of a partially fissured cavity. It has been suggested to use a stereometric method with scan heads separated by a given distance. The surface of the cavity to be scanned, the so-called scan area, is illuminated via an illumination device on the scan head and the scan area of the cavity is thus to be scanned.

However, despite the sophisticated scanner, the scan result is often unsatisfactory, so that it has been tried to further improve the scan head in a correspondingly expensive way. Nevertheless, the tests carried out so far in this respect, especially in the case of three-dimensionally complicated cavities, did not yield satisfactory results.

Nevertheless, in order to allow reasonably precise detection of the surface of the cavity, i.e. the scan area, it has already been suggested to work with different frequency ranges of the electromagnetic radiation. With a moist surface, for example, it can be advantageous to use visible light or UV light. On the other hand, the reflective properties of certain materials that can make up the cavity are better while using both ultrasound and X-rays.

A disadvantage herein resides that scanners having different frequency ranges are required to be provided, which overall makes the solution more expensive and sometimes no longer practicable.

These solutions are basically suitable for recording the static situation in the mouth. However, it lacks a solution for the functional impression, i.e. the impression of the oral situation taking into account deformation of mouth parts in different positions of the lower jaw to the upper jaw.

An attempt has been made to take an impression at different positions or at two different opening positions of the mouth. On the whole, the movement pattern is extremely complex due to the different anatomical features of the condylar joints and therefore not so easily accessible to digitization.

SUMMARY OF THE INVENTION

Contrary to this, the object of the invention is to provide a recording device as well as a method for operating a recording device according to the attached claims, which are also suitable for functional impressions, and, in any case, are significantly better than the recording devices of prior art.

This object of the invention, will be achieved according to the attached claims. Advantageous embodiments will arise from the subclaims.

According to the invention it is provided for the film-like material to spread in a balloon-like manner extending in particular across an alveolar ridge in the mouth of a patient, but also in the remaining oral cavity. A first scan head is inserted into this balloon. If the balloon is overpressurized, it is in contact with the scanning area, e.g. the edentulous alveolar ridge of the patient. The overpressure deforms soft tissue, while hard tissue such as existing teeth will not be deformed or will not really be deformed.

Herein, the term scan head can be used to refer to any type of detection device that can be used directly or indirectly to generate a 3D model of the scanned object, e.g. a scan head using the Doppler effect, also known as OCT, electromagnetic radiation, e.g. visible or invisible light or X-rays, in particular an array of CCD chips, or ultrasound.

The extent of deformation depends on the overpressure applied. If overpressure is increased, stronger deformation occurs. It is intended to perform deformation using the appropriately selected overpressure, so that the scanning device will be able to detect whether soft tissue or hard tissue is present in the scan areas in question.

For this purpose, a pattern is preferably applied to the film-like material. The pattern can be seen from the first scan head and deformation due to pressurizing the film-like material can be detected.

According to the invention, it is provided for a second scan head to be spaced apart from the first scan head. Alternatively, it is also possible to create a scan head having several scan units, whereof one is arranged intraorally and the other one is arranged extraorally, so that the anatomical conditions in the mouth and outside the mouth can simultaneously be recorded. While the first scanning head is preferably located in the balloon in the patient's mouth, the second scanning head is located outside the patient's mouth and is directed towards it. Alignment is such that the scanning axis is substantially aligned with the first scan head.

It is also possible to use different scanning procedures for the intraoral and extraoral scan heads. For example, a scan head with optical coherence tomography (OCT) could be used intraorally or as a first scan head, and a stereoscopic scan head could be used extraorally.

The detection area extends around this scanning axis, for example, such that at least the area of the patient's lips can be fully detected. It is also possible to significantly extend the scan area beyond this area, e.g. if the tragus or a marking element on the tragus and/or the bipupillary line is to be detected. If, for example, the second scanning head is positioned at a distance of 10 cm, a scanning angle of +/−45 degrees in each direction is sufficient to fully cover the patient's mouth.

According to the invention, the second scan head detects how the tissue surrounding the patient's mouth, especially the lips, deforms while the balloon is inflated.

The data obtained in this way, i.e. intraoral data based on the first scan head and extraoral data based on the second scan head, are only summarized electronically and the overall view subsequently shows how the patient's soft tissue is deformable in the mouth area.

Detection is preferably performed such that the balloon is inflated gradually and each of the corresponding 3D data are then acquired and, for example, are acquired at ⅓ nominal pressure, ⅔ nominal pressure or the full nominal pressure.

In an advantageous embodiment, it is provided for the pressure in the balloon to be slightly reduced, e.g. to 80% of the nominal pressure. The patient then has to perform so functional movements, which compress the balloon. These movements are recorded by both scanning heads, or the resulting deformations of the soft tissue are recorded.

The intraoral or first scan head now records the points of movement of the pattern and the film-like tissue, the corresponding functional movements corresponding to the movements the patient makes.

It may eventually be necessary to regulate the pressure in the balloon, as air displacement imposed by the movement should be compensated.

According to the invention, the extraoral scanner preferably detects deformation of the soft tissue extraorally surrounding the mouth. In addition, the occlusal plane can also be detected, for example, by additionally detecting the pupils and a marker attached to the tragus. In this preferred embodiment, the detection areas of the extraoral scan head are appropriately selected so that the patient's eye/ear region can also be covered.

Based on the scan results of both scan heads during the functional movements, a digital functional model is then created which not only records the masticatory movements, but also the relevant area of the patient's head.

The occlusion plane can be used as a reference point for the tooth set-up based on the distance between the center of the lips and the tragi corresponding to the scanning of the extracorporeal scan head. Deformation of the lips and cheeks allows adaptation to the patient-specific anatomy during the fabrication of a prosthesis. The chin movements recorded can also be used to optimize the tooth set-up.

While the extraoral scan head can be used, according to the invention, to acquire and visualize the lip fullness, but also aesthetic lines such as the midline, canine line, smile line and lip closure line, the intraoral scanner acquires the functional margin and surface of the edentulous jaws.

The jaw relation can be determined by simultaneously scanning the upper and lower jaw. According to the invention, it is advantageous to work with variable pressure during the scanning process of both scan heads.

If the internal pressure in the balloon is reduced, the patient tends to reduce the mouth opening angle on his own. Corresponding movements of the patient's jaws relative to each other result in a change in the indentation pattern or the indentation depth of the film-like material.

For this purpose, an appropriate pattern can be applied to the film-like material. It is also possible to rather use a web or other flat material, which is suitable to be detected by at least one scan head.

According to the invention, realization of two scan heads also allows a three-dimensional image at least in the area that essentially extends between the scan heads, i.e. the area of the anterior/canine teeth as well as the corresponding mucous membranes and the lips.

While deformability measurement is preferably realized by using a single balloon, it is also possible in an alternative embodiment, to rather divide the balloon into a balloon having several chambers. They can be filled independently of each other, so that different mouth regions of the patient can each be filled with air.

According to the invention, it is provided to place the first scan head on a scan head carrier. The second scan head can also be mounted on the same scan head carrier or on a separate scan head carrier. The first scan head is provided for an all-round scan, i.e. for acquiring an image that spherically extends around the scan head. Thus, a scan area at least partially extends around the scan head.

A film-like material in the manner of a balloon is attached to the scanning area. It is overpressurized, which is possible, as the balloon forms a closed and deformable body.

The way in which the overpressure can be generated can, in any way, be adapted to the requirements. In this respect, a small hand pump is preferred, via which the operator can specifically generate a specified overpressure. Alternatively, it is also possible to implement a mechanical pump, in particular an automatically pressure-controlled pump. It can be connected to a manometer and/or a drain valve so that specific overpressure values can also be set.

In this embodiment, the balloon and the first scan head are intraorally arranged. It is to be understood that an equivalent can also be realized using a patient head model simulating the tissue of the patient.

Due to the overpressure, the film-like material deforms a soft tissue which is pressurized by the balloon.

Another scan head is provided spaced apart from but focused to the patient's mouth opening. This scanning head detects movements of the patient's lips, mouth and even the entire lower face. To facilitate detection, markings may be provided in and on the patient's mouth in any manner.

It is to be understood that any other markings, for example in the region of the tragi, and in any other places, are also possible.

It is also possible to configure the balloon or a separate chamber of the balloon such that it covers and fills the region of the oral vestibule. This requires an appropriate shape of the balloon, which follows the shape of the alveolar process. If necessary, a third scan head can also be formed here or one of the two other scan heads can be moved to this position.

The film-like material is preferably realized as a disposable article and can also be produced at low cost.

Basically, a standard balloon with a corresponding imprint can be used to provide a sample. Such a balloon, while being orally accommodated, is pressure resistant in a suitable way, for example up to 1 bar, and then deforms the soft tissue to which it is attached without further intervention.

The detection spectrum of the scan heads can be the same or different. Any suitable electromagnetic radiation is possible herein, for example UV light, visible light, infrared light, X-rays. However, it is also possible to acquire data using ultrasound and, if required, a scan head can also be implemented using the Doppler Effect.

The technical measures for realizing scan heads are to be understood only as examples, and are non-limiting.

According to the invention, it is also advantageous that the second scan head extraorally acquires the patient's image from the front when the balloon is being pressurized intraorally. The scan head recognizes where soft tissue is present and where deformation by hard tissue is prevented or limited, regardless of chewing movements.

BRIEF DESCRIPTION OF THE DRAWING

Further details, advantages and characteristics of an example of the invention can be found in the following description, while making reference to the drawing.

The only FIGURE in the drawing—FIG. 1—shows a recording device according to the invention while being in use, in a first embodiment.

DETAILED DESCRIPTION

From FIG. 1, a schematic representation of a scanning device 10 according to the invention may be seen. It comprises a balloon 12 which consists of a balloon film 14 which forms the elastically stretchable material. The balloon 12 has a balloon outlet 16 in a manner known per se. A scan head carrier 18 passes through this outlet, holding a scan head 20 within the balloon and guiding it in a safe manner.

Several scanners are attached to the scan head 20, two of which scanners 22 and 24 being shown herein. A multitude of scanners can actually be provided, for example 100, while in case of a small number of scanners, it is preferred that they preferably are movably mounted at the scan head 20.

The scanners are to acquire the complete interior space of the balloon film 14. The balloon film 14 comprises a reference pattern 26 that, in the embodiment shown, is formed in the type of a web that can extend in even line spacing, or more preferably can extend unevenly across the balloon film. Especially if the line spacing is even, it is also possible to encode the lines, e.g. to dot them, i.e. to provide them with a unique dash-dot sequence, so that each line can be identified even if the position of the scan head changes.

The scan head carrier 18 is surrounded by a seal that seals the balloon outlet 16 against the ambient air.

A control device 44 is provided outside the balloon. In any case, this device evaluates the images acquired by the scanners and also controls an overpressure P which inflates the balloon 12.

Through inflation, the balloon film 14 closely and exactly follows the contour of a cavity 40. The reference pattern 26 thus extends along a scan area 42 in a deformed state. From the deformation of the reference pattern 26, the shape of the scan area can be calculated in detail according to the invention.

In an advantageous embodiment, the balloon 12 is inflated such that it completely abut the inner surface of the cavity. By reducing the volume of the cavity, further increase in pressure occurs, which can be detected by the scan head 20.

The scan head 20 can be operated in any suitable wavelength range. Electromagnetic radiation such as light radiation, is conceivable, for which an additional light source is preferred, which illuminates the balloon's interior and is attached to the scan head 20. The use of X-rays or ultrasound is also possible instead or in addition.

In another embodiment it is conceivable to first insert a scanning accessory means which is transparent to the scanning radiation, into the cavity and to then cure it.

The scanning accessory means has an insertion aperture for a scan head. It is cured in cavity 40, thereby deforming the reference pattern applied to the surface of the scanning accessory means. Subsequent to at least being partially cured, it is removed—if required by elastic compression or by opening the cavity—and subsequently the scan head is inserted into the scanning accessory means and the surface of the scanning accessory means is scanned from the inside.

According to the invention, realization of a second scan head 43 is provided extraorally, in addition to the first scan head 20. In the example as illustrated, the second scan head 43 is mounted on the same scan head carrier 18 outside the film-like material 14. Both scan heads are mounted externally or are supported on the patient's mouth.

It is to be understood that instead a stationary holder can also be provided, which carries and supports the first and/or second scan head 43, so that the patient must actively approach this arrangement to enable scanning.

Both scanning heads are electrically connected and are also connected from the control towards a control device 44 that starts and runs the scanning processes either automatically or after intervention of the operator, but also evaluates the images acquired, and combining the results obtained in a way appropriate to each individual patient.

The scan head 43 is aligned towards the scan head 18, acquiring the image of the closed/open/semi-open mouth of the patient, especially including the lips 46 and 48, but preferably also beyond that, for example up to the region of the ears of the patient.

The angle of coverage can be broadly be adapted according to the requirements. It is also possible to connect a focusing device upstream of the second scan head, which, in the manner of a variable wide-angle lens, provides the necessary image section.

Preferably, marking elements 50 and 52 are attached to the tragus, on the lips and/or in the alveolar region when the mouth is half-opened, the positions of which are detectable by the second scan head 43.

In any case, the second scan head 43 also records functional movements performed by the patient, thus enabling a functional scan to provide dynamic data for the prosthesis/prostheses to be manufactured.

In order to provide the desired overpressure, a pressure source 54 comprising a pressure hose 56 is provided, which is connected to the balloon 12 and pressurizes it so that, in the oral cavity, abuts against the tissue located therein, the so-called scan area.

According to the invention, different pressure levels of the balloon are now being acquired by the scan heads 20 and 43. Alternatively, the patient can be asked to compress the balloon 12 by closing the mouth.

This also results in deformation of the adjacent soft tissue and thus the possibility of analyzing and determining the tissue distribution according to the invention.

The invention claimed is:

1. A recording device arrangement comprising
a first scan head which is mounted on a scan head carrier, the first scan head being designed for scanning an intraoral scan area which extends at least partially around the first scan head, and
a film-like material, wherein the film-like material in the manner of a balloon, deforms when the film-like material is at least partially under pressure and/or adhered to the scan area, and
wherein a second scan head for scanning extraorally is spaced apart from the first scan head for scanning deformations during pressure application to the film-like material, which deformations occur in a substance intraorally or extraorally,
wherein the first scan head is located within the film-like material and the second scan head is located outside the film-like material.

2. The recording device arrangement according to claim 1,
wherein the substance is formed as a tissue comprising lip tissue and/or cheek tissue, and
wherein the first and/or the second scan head detects a change in shape and/or the resilience of the substance, and/or the film-like material comprises patterns which can be scanned by the first scan head.

3. The recording device arrangement according to claim 1,
wherein the scan head carrier has at least two scan head accommodations, and
wherein one scan head accommodation is always equipped with the first scan head and the other scan head accommodation can optionally be equipped with the second scan head.

4. The recording device arrangement according to claim 1,
wherein the first scan head is essentially designed as an all-round scan head having an essentially spherical detection space and
wherein the second scan head is designed as a directional scan head detecting significantly less than one hemisphere comprising a cone of approximately 120 degrees expansion.

5. The recording device arrangement according to claim 1,
wherein the second scan head comprises a scanning axis that is substantially aligned towards the first scan head with a deviation of less than 30 degrees.

6. The recording device arrangement according to claim 1,
wherein the first and second scan heads are each accommodated on a common scan head carrier in a spaced apart and precisely defined position in a scan head reception.

7. The recording device arrangement according to claim 1,
wherein the film-like material which at least partially surrounds the first scan head is replaceably mounted and
wherein the first scan head can be passed through an opening in the film-like material.

8. The recording device arrangement according to claim 1,
wherein the film-like material is compressible after being brought to a predetermined pressure by decreasing a cavity surrounding the scan area and
wherein the first scan head detects the movement of the scan area as a function of the existing pressure.

9. The recording device arrangement according to claim 1,
wherein the recording device comprises a control and evaluation device detecting and evaluating scan results in relation to the respective pressure applied to the film-like material.

10. The recording device arrangement according to claim 1,
wherein at least two inflation modes or printing modes of the film-like material are each used as a base for a scanning operation, and
wherein a control and evaluation device of the recording device detects individual parts of the scanning area between the two modes and/or detects differences between the two modes.

11. The recording device arrangement according to claim 1,
wherein a digital model of a patient's head is produced based on a plurality of scanning operations of the first and/or the second scan head regarding anatomical conditions and resilience of the respective tissue affected, which anatomical conditions and resilience of the respective tissue affected form the scanning region.

12. The recording device arrangement according to claim 1,
wherein each scanning head provides for detection using UV light, visible light and/or infrared light and/or ultrasound and/or X-rays, separated by different spectra.

13. The recording device arrangement according to claim 1,
wherein a control and evaluation device is provided in the recording device by the use of which a bipolar line including at least one reference marker can be detected by an extraoral scan head.

14. The recording device arrangement according to claim 1,
wherein the recording device has a control and evaluation device by the use of which the anatomical conditions and/or a deformation of the lips and the surrounding region of a patient can be detected when the film-like material is placed under intraoral pressure according to the type of film-like material.

15. A method for operating a recording device comprising a first scan head mounted on a scan head carrier, the first scan head located within a film-like material, the first scan head having a scanning region extending at least partially around the first scan head and a second scan head arranged spaced apart from the first scan head on the scan head carrier, the method comprising,
pressurizing the film-like material so as to abut the scanning region due to pressure and/or adhesion, wherein the film-like material is at least partially deformed, and
wherein the second scan head scans extraorally, extends extraorally, and scan deformations in the film-like material that occur in a substance intraorally or extraorally.

* * * * *